United States Patent [19]

Vincent

[11] 4,172,805
[45] Oct. 30, 1979

[54] BENZYLOXY ENDBLOCKED ORGANOSILICON DIELECTRIC FLUIDS AND ELECTRICAL DEVICES CONTAINING SAME

[75] Inventor: Gary A. Vincent, Midland, Mich.

[73] Assignee: Dow Corning Corporation, Midland, Mich.

[21] Appl. No.: 881,451

[22] Filed: Feb. 27, 1978

[51] Int. Cl.$^2$ .............................................. H01B 3/18
[52] U.S. Cl. ................................ 252/63.7; 252/63 S; 174/110 S; 260/448.2 B
[58] Field of Search ........................... 252/63 S, 63.7; 260/448.2 B

[56] References Cited

U.S. PATENT DOCUMENTS 3,909,434  9/1975  Brown .................................. 252/63.7

OTHER PUBLICATIONS

Chemical Abstracts, vol. 57 (10), col. 12525h.

Primary Examiner—John D. Welsh
Attorney, Agent, or Firm—Jack E. Moermond

[57] ABSTRACT

Disclosed are benzyloxy substituted organosilicon compounds having a viscosity of from about 5 to about 500 cs at 25° C. and useful as dielectric fluids. Disclosed also are improved electrical devices such as transformers and capacitors containing such compounds as dielectric fluids.

21 Claims, No Drawings

BENZYLOXY ENDBLOCKED ORGANOSILICON DIELECTRIC FLUIDS AND ELECTRICAL DEVICES CONTAINING SAME

BACKGROUND OF THE DISCLOSURE

In numerous electrical devices it is necessary to provide a liquid insulating medium which is called a "dielectric fluid." This liquid has a substantial higher breakdown strength than air and by displacing air from spaces between conductors in the electrical equipment or apparatus, materially raises the breakdown voltage of the electrical device. With the ever increasing sophistication of electrical equipment, the various electrical devices are operating at higher and higher voltages. This means that the dielectric fluids used in such devices are subjected to greater and greater stresses. These problems have, of course, necessitated the search for improved dielectric fluids.

By way of illustration, corona or partial discharge is a major factor causing deterioration and failure of capacitors or other power factor correction devices. A capacitor operating in corona will have a life of only minutes or hours instead of the expected 20 years. A capacitor properly impregnated with a suitable dielectric fluid will be essentially free of corona discharge to a voltage of at least twice the rated voltage. During use, when a dielectric fluid is placed under increasing stress a point is reached where breakdown occurs. The voltage at which the capacitor will suddenly flash into corona is known in the art as the corona inception voltage (CIV). This voltage is dependent upon the rate at which the voltage is applied. There is considerable difference between the sensitivity of different fluids to the rate of rise of voltage. The corona will, however, extinguish with a reduction of voltage. The corona extinction voltage (CEV) is not a fixed value for each fluid but is a function of the intensity of corona before the voltage is reduced. For best results both the CIV and CEV should be as high and as close together as possible.

With the exception of certain special applications, the polychlorinated biphenyl compounds (generally known as "PCB's") have been the standard dielectric fluid in electrical devices since the 1930's when the PCB's replaced mineral oil. Various other liquids including some siloxanes have also been suggested for use as dielectric fluids. See, for example, U.S. Pat. Nos. 2,377,689 and 3,838,056 and British Pat. Nos. 899,658 and 899,661. Recently the PCB's have lost favor in the sight of the environmentalists and efforts are being made worldwide to find suitable replacements for the PCB's.

Among the dielectric materials proposed as suitable replacements for PCB's are polyorganosiloxanes such as dimethylpolysiloxanes, methylphenylpolysiloxanes, phenoxy substituted methylphenylsilanes and siloxanes (e.g., U.S. Pat. No. 3,909,434), monochloroalkylsiloxanes (e.g., U.S. Pat. No. 3,838,056) and nitroarylsiloxanes (e.g., U.S. Pat. No. 3,900,416), employed either alone or in combination with various additive fluids such as soluble chlorendates (U.S. Pat. No. 3,948,789), ketones (U.S. Pat. No. 3,984,338) and the like. Unfortunately, these proposed "replacement" materials are frequently unacceptable in terms of one or more of the requisite high CEV and CIV values, and viscosity, flammability or fire point characteristics.

As one example, the electrical performance capability and high flash and fire points of 50 centistoke dimethylpolysiloxane fluid appear to make it well suited for use as a dielectric fluid in transformers. Such a silicone fluid is not readily usable in high stress ($\geq$1000 volts/mil) capacitors, however, because of its relatively low CEV of about 600 volts/mil. Put another way, once corona discharges are initiated in such a fluid, they will not extinguish because the operating stress substantially exceeds the CEV of the fluid and failure of the capacitor is certain to follow rapidly. As another example, use of volatile, low molecular weight organic additives may "fortify" the siloxane but substantially diminish desired flammability characteristics.

Specifically incorporated by reference herein is the disclosure of co-owned, co-pending U.S. Application Ser. No. 836,448 filed Sept. 26, 1977, now U.S. Pat. No. 4,147,646, relating to novel capacitors including, as dielectric fluids, naphthoxy substituted siloxane fluids having a viscosity of less than about 50 centistokes at 25° C. Also incorporated by reference herein is the disclosure of co-owned U.S. Application Ser. No. 881,452 of applicant, filed concurrently herewith and relating to novel furfuryloxy substituted silanes and siloxanes and electrical devices including the same as dielectric fluids.

BRIEF SUMMARY

According to the present invention, there are provided relatively low viscosity benzyloxy substituted organosilicon compounds—including certain novel benzyloxy substituted siloxanes—and electrical devices, such as capacitors, transformers, cables and the like, having such compounds as dielectric fluids. Certain of the organosilicon compounds providing useful dielectric fluids for electrical devices are benzyloxy substituted silanes of the general formula:

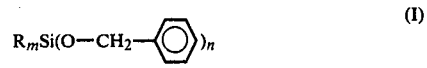

(I)

wherein R is selected from the group consisting of monovalent hydrocarbon radicals having from 1 to 10 carbon atoms, m has a value of 1 to 3, n has a value of 1 to 3, and m+n=4.

Novel siloxanes of the invention providing dielectric fluids for use in electrical devices include "linear" benzyloxy endblocked siloxanes of the general formula:

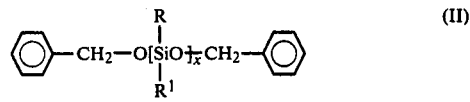

(II)

wherein R and $R^1$ are the same or different and selected from the group consisting of monovalent hydrocarbon radicals having from 1 to 10 carbon atoms, and x has a value from about 2 to about 100 and preferably less than about 25.

Additional novel siloxanes include "branched" benzyloxy endblocked siloxanes of the general formula:

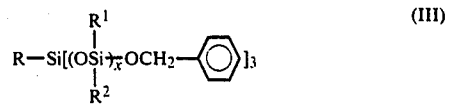

(III)

wherein R, $R^1$ and $R^2$ are the same or different and selected from the group consisting of monovalent hydrocarbon radicals having from 1 to 10 carbon atoms and x has a value of from about 1 to about 35 and preferably less than about 10.

Still other novel siloxanes include trihydrocarbyl endblocked, benzyloxy substituted siloxanes having the general formula:

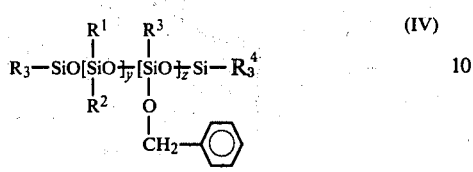

wherein R, R¹, R², R³ and R⁴ are the same or different and selected from the group consisting of monovalent hydrocarbon radicals having from 1 to 10 carbon atoms and y and z each have a value of from about 1 to about 50 and preferably less than about 10.

Electrical devices of the invention include both transformers and capacitors as well as other devices such as electrical cables, rectifiers, electromagnets, switches, fuses, circuit breakers and as coolants and insulators for dielectric devices such as transmitters, receivers, flyback coils, sonar buoys, toys and miltary "black boxes." The methods for employing the dielectric fluids in these various applications (be they, for example, as a reservoir of liquid or as an impregnant) are well known to those skilled in the art. For best results, the viscosity of the dielectric fluids of the invention should be in the range of 5 to 500 centistokes at 25° C. If the viscosity exceeds 500 centistokes they are difficult to use as impregnants and at less than 5 centistokes their volatility becomes a problem unless they are used in a closed system. Further, when dielectric fluids are incorporated in capacitors according to the invention, it is preferred that the fluids have a viscosity of less than about 50 centistokes.

Other aspects and advantages of the present invention will be better understood upon consideration of the following detailed description.

DETAILED DESCRIPTION

Preferred dielectric fluids of the invention include benzyloxy substituted silanes and siloxanes of formulas I through IV above, wherein the substituent groups variously designated as R, R¹, R², R³ and R⁴ are hydrocarbyl groups such as alkyl radicals including methyl, ethyl, propyl, ispropyl, butyl, isobutyl, t-butyl, amyl, hexyl, heptyl, and octyl, or cyclic, saturated or unsaturated, radicals such as phenyl. It is expected that the most suitable fluids from a standpoint of viscosity characteristics and expense of synthesis are those wherein all substituents are the same and lower alkyl, e.g., methyl. Also suitable are the benzyloxy substituted siloxanes wherein each repeating siloxane unit is diphenyl or methyl and phenyl substituted. Consistent with the above, preferred formula I silanes of the invention include dimethyldibenzyloxysilane and methyltribenzyloxysilane. Preferred formula II linear siloxanes of the invention include those of the exemplary formulas:

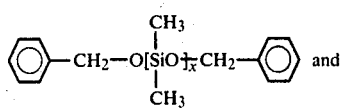

and

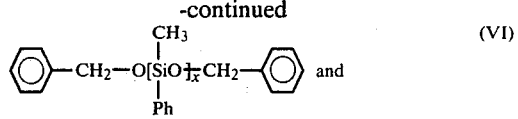

and

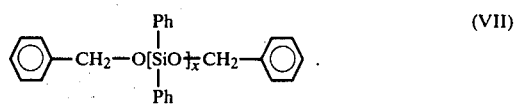

In a like manner, preferred formula III branched siloxanes according to the invention may be methyl substituted compounds of the formula:

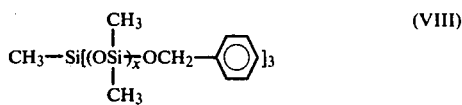

or may be phenyl substituted or methyl and phenyl substituted. Lastly, preferred formula IV compounds according to the invention include the methyl substituted compounds of the formula:

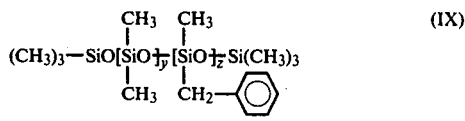

or may be phenyl substituted or phenyl and methyl substituted.

Silanes according to the invention may be prepared according to procedures well known in the art including, for example, reacting benzyl alcohol and alkoxy (e.g., methoxy) substituted silanes such as methyltrimethoxysilane and dimethyldimethoxysilane. Siloxanes according to the invention may be prepared by equilibrating/condensing benzyl alcohol and suitable polysiloxane cyclic materials. Alternatively, benzyl alcohol may be reacted with suitable alkoxy endblocked polysiloxanes, which in turn are produced by equilibrating alkoxy silanes with polysiloxane cyclics. Lastly, the siloxanes may be prepared by reacting benzyloxy substituted silanes of formula I with cyclic polysiloxanes. Various other preparatory techniques will be readily apparent to those skilled in the art who will consider and balance various properties of reagents and reactants such as the relative incompatibility of benzyl alcohol with acid catalysts, the relative suitability of various organic salts (e.g., tetramethylguanadine trifluoroacetate), organometallics (e.g., tetrabutyl titanate), and bases (e.g., sodium methoxide) as transesterification catalysts, and the relative costs of the selected siloxane and silane starting materials.

The following examples of practice of the invention are provided for illustrative purposes and provide no limitation upon its scope. All viscosities referred to herein were measured at 25° C. unless otherwise specified.

EXAMPLE I

To a glass reaction vessel there was added 19.5 g of dimethyldimethoxysilane, 180.5 g of dimethylcyclosiloxanes, and 5 drops of trifluoromethane sulfonic acid. These materials were thoroughly mixed and then allowed to stand at room temperature for 48 hours to produce a methoxy endblocked polydimethylsiloxane fluid. Then 60 g of benzyl alcohol and 0.5 g of tetramethylguanidine trifluoroacetate were added to the reaction vessel and the mixture heated at reflux temperature for one hour. A Dean-Stark trap was attached and volatiles (mainly methanol) were collected as the reaction temperature was increased to 250° C. The reaction mixture was then cooled and 5 g of calcium oxide added. The liquid was then stripped to 270° C. at 0.2 mm of mercury pressure to give 80 g of volatiles and 120 g of residue. The residue was agitated with fuller's earth and vacuum filtered to obtain, as a clear, colorless liquid, benzyloxy substituted dimethylsiloxane having the general formula:

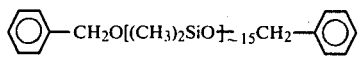

This fluid was found to have a viscosity of 18 centistokes, a dielectric constant of 2.92 at 100 Hertz and $10^5$ Hertz, a dissipation factor of 0.00021 at 100 Hertz and zero at $10^5$ Hertz, and a volume resistivity of $1.4 \times 10^{14}$ ohm-centimeters.

A small 0.01 μf test capacitor of composite film/paper construction (2 0.0005 inch polypropylene films and a 0.0004 inch paper wick to provide a 0.0014 inch total barrier thickness) was impregnated in a 1 ounce round vial with the above prepared dielectric fluid. A small glass funnel was placed in the vial and the vial was centered in a 2 liter resin kettle by a fabricated wire bracket. The test dielectric fluid composition was contained in a 125 mil pressure equalizing dropping funnel over the center of the capacitor vial. The temperature within the kettle was raised to and maintained between 85° and 90° C. with a temperature controlled external heating mantle.

Vacuum on the above system was obtained with a mechanical forepump and a mercury vapor diffusion pump. Pressure would quickly drop to about 150 microns Hg and would continue to drop slowly for about 24 hours. Final pressure would be below 10 microns Hg. (Note: Pressure must be measured in the kettle and not at the pump inlet. Differences of over 100 microns Hg pressure were frequently observed). Vacuum was maintained for 4 days prior to dropping the test dielectric fluid into the capacitor. After the fluid was dropped vacuum was maintained for at least 30 minutes.

The corona inception voltage of a capacitor tested immediately after removal from the vacuum chamber is usually very low. This indicates a lack of complete permeation of films and possibly some remaining dry spots in the capacitor. Permeation will continue after the above impregnation procedure is completed. With the compositions of this invention heating of the impregnated capacitor for several hours at 85° C. is desirable to achieve good permeation and satisfactory corona inception voltage values. The time for complete permeation at room temperature with the compositions of this invention has not been determined, however some literature references mention periods of about 3 months at room temperature for the currently used polychlorinated biphenyls.

The corona inception voltage reported was obtained by raising the voltage steadily at about 200 to 300 volts per second until corona was detected. The voltage was then reduced to an arbitrary value and, if the corona extinguished, the capacitor was rested for at least 5 minutes. After resting the capacitor was retested selecting a higher voltage to test for extinction.

In this test capacitor the above prepared benzyloxy substituted dimethylsiloxane fluid had a corona inception voltage of 3200 volts per mil and a corona extinction voltage of 1800 volts per mil. By way of comparison, a trimethylsilyl endblocked polydimethylsiloxane having a viscosity of 50 centistokes, which is a typical dielectric fluid, would generally have a corona inception voltage of 2600 and a corona extinction voltage of 500 in the same capacitor test.

EXAMPLE II

A mixture of 175 g of dimethylcyclosiloxanes, 51 g of benzyl alcohol, 10 drops of trifluoromethane sulfonic acid, and 100 ml of toluene was heated at reflux under a Dean-Stark trap. When the theoretical 4.25 ml of water had been collected after two hours of reaction time, 5 g of calcium oxide was added to the reaction vessel. The liquid was then stripped to 250° C. at 0.3 mm of mercury pressure. The 115 g of residue left after stripping was agitated with fuller's earth and then vacuum filtered to obtain a crystal clear, colorless benzyloxy substituted dimethylsiloxane having the general formula:

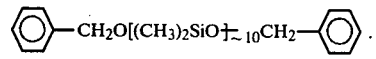

This fluid was found to have a dielectric constant of 2.91 at 100 Hertz and $10^5$ Hertz, a dissipation factor of 0.00623 at 100 Hertz and zero at $10^5$ Hertz, and a volume resistivity of $1.9 \times 10^{12}$ ohm-centimeters. In the capacitor test described in the previous example, the above prepared benzyloxy substituted dimethylsiloxane fluid had a corona inception voltage of 3200 volts per mil and a corona extinction voltage of 1900 volts per mil.

EXAMPLE III

In a one liter, one-necked flask there was placed 356 g of benzyl alcohol, 149 g of methyltrimethoxysilane, and a catalytic amount of sodium methoxide. The reaction mixture was heated at reflux for one hour and then a Dean-Stark trap was added to collect methanol. When the theoretical amount of methanol had been collected the flask was connected to a vacuum system and the portion boiling in the range of 210°–220° C. at 0.3 mm of mercury pressure was collected. About 355 g of the product

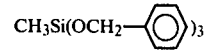

was obtained. This product was found to have a dielectric constant of 3.60 at 100 Hertz and 3.61 at $10^5$ Hertz, a dissipation factor of 0.00625 at 100 Hertz and 0.00005 at $10^5$ Hertz, and a volume resistivity of $4.6 \times 10^{12}$ ohm-centimeters. In the capacitor test described in Example I this fluid had a corona inception voltage of 3200 volts per mil and a corona extinction voltage of 2800 volts per mil.

EXAMPLE IV

A mixture of 201 g of dimethylcyclosiloxanes, 99 g of methyltribenzyloxysilane, and 1 g of potassium silanolate (neutralization equivalent about 450) were heated at 160° C. for about 65 hours. The reaction mixture was treated with 2 g of sodium bicarbonate and then stripped to 260° C. at 0.1 mm of mercury pressure to obtain 123 g of volatiles and 175 g of liquid residue. This residue was agitated with fuller's earth and then vacuum filtered to obtain, as a light yellow liquid, benzyloxy substituted dimethylsiloxane having the general formula:

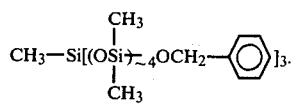

This fluid was found to have a viscosity of 21 centistokes, a dielectric constant of 3.06 at 100 Hertz and $10^5$ Hertz, a dissipation factor of 0.00046 at 100 Hertz and 0.00003 at $10^5$ Hertz, and a volume resistivity of $4.5 \times 10^{13}$ ohm-centimeters. In the capacitor test described in Example I, this fluid had a corona inception voltage of 3200 volts per mil and a corona extinction voltage of 2200 volts per mil.

EXAMPLE V

A fluid having the general formula,

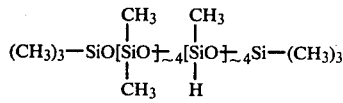

was prepared by the acid catalyzed equilibration of hexamethyldisiloxane, trimethyl-endblocked methyl hydrogen polysiloxane and dimethylcyclosiloxanes. A 150 gram quantity of the fluid, 100 g benzyl alcohol, and three drops of 0.1 N $H_3PtCl_6$ in isopropanol was heated to 60° C. Gas evolution was so rapid that some of the reaction mixture bubbled out of the reaction flask through the top of a water condenser. Without being heated, the reaction temperature increased to 100° C. and the reaction was allowed to proceed overnight without additional heating. The following morning, three ml of triethyl amine were added; and, the reaction mixture was stripped to 250° C. at 1.0 mm of mercury pressure to give a residue which was agitated with fuller's earth and then vacuum filtered to obtain benzyloxy substituted siloxane of the general formula:

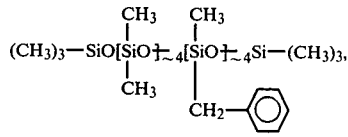

having a viscosity of about 31.5 centistokes. The dielectric constant of the fluid was 3.5 at 100 Hertz, and the dissipation factor was of 0.0055 at 100 Hertz. In the capacitor test described in the previous example, the above-prepared fluid had a corona inception voltage of 2700 volts per mil and a corona extinction voltage of 1700 volts per mil.

Numerous modifications and variations in practice of the invention are expected to occur to those skilled in the art upon consideration of the foregoing description. As one example, electrical devices of the invention may be manufactured to include the above-described silanes and siloxanes as from about 10 to about 100 percent of the total dielectric fluid content. With respect to the silanes and siloxanes prepared according to the invention, the extent of benzyloxy substitution is subject to some degree of variation, with two benzyloxy substituents being preferred on siloxanes of formula II, three such substituents for siloxanes of formula III, one to three such substituents for silanes of formula I, and up to ten benzyloxy substituents for siloxanes of formula IV. Therefore only such limitations as appear in the appended claims should be placed thereon.

What is claimed is:

1. An article of manufacture consisting of an electrical device including a dielectric fluid comprising a benzyloxy substituted organosilicon compound having a viscosity of from about 5 to about 500 centistokes at 25° C. and having the formula

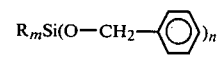

wherein R is selected from the group consisting of monovalent hydrocarbon radicals having from 1 to 10 carbon atoms, m has a value of 1 to 3, n has a value of 1 to 3, and m+n=4.

2. The article of claim 1 in which R is methyl.
3. The article of claim 1 in which R is phenyl.
4. The article of claim 1 in which m has a value of 2.
5. The article of claim 1 in which m has a value of 1.
6. An article of manufacture consisting of an electrical device including a dielectric fluid comprising a benzyloxy substituted organosilicon compound having a viscosity of from about 5 to about 500 centistokes at 25° C. and having the formula

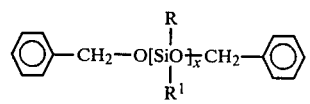

wherein R and $R^1$ are the same or different and selected from the group consisting of monovalent hydrocarbon radicals having from 1 to 10 carbon atoms, and x has a value from about 2 to about 100.

7. The article of claim 6 in which R and $R^1$ are both methyl.
8. The article of claim 6 wherein R is phenyl and $R^1$ is methyl.
9. The article of claim 6 in which x is less than about 25.
10. An article of manufacture consisting of an electrical device including a dielectric fluid comprising a benzyloxy substituted organosilicon compound having a viscosity of from about 5 to about 500 centistokes at 25° C. and having the formula

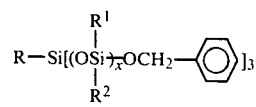

wherein R, $R^1$ and $R^2$ are the same or different and selected from the group consisting of monovalent hydrocarbon radicals having from 1 to 10 carbon atoms and x has a value of from about 1 to about 35.

11. The article of claim 10 in which R, $R^1$ and $R^2$ are all methyl.

12. The article of claim 10 in which R and $R^1$ are methyl and $R^2$ is phenyl.

13. The article of claim 10 in which R and $R^1$ are phenyl and $R^2$ is methyl.

14. The article of claim 10 in which x is less than about 10.

15. An article of manufacture consisting of an electrical device including a dielectric fluid comprising a benzyloxy substituted organosilicon compound having a viscosity of from about 5 to about 500 centistokes at 25° C. and having the formula

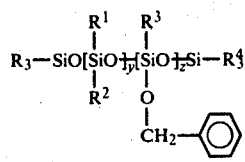

wherein R, $R^1$, $R^2$, $R^3$ and $R^4$ are the same or different and selected from the group consisting of monovalent hydrocarbon radicals having from 1 to 10 carbon atoms and y and z each have a value of from about 1 to about 50.

16. The article of claim 15 in which R, $R^1$, $R^2$, $R^3$ and $R^4$ are all methyl.

17. The article of claim 15 in which R, $R^1$, $R^3$ and $R^4$ are methyl and $R^2$ is phenyl.

18. The article of claim 15 in which R, $R^1$, $R^2$, and $R^4$ are methyl and $R^3$ is phenyl.

19. The article of claim 15 in which y and z each have a value of less than about 10.

20. An article of any of claims 1, 6, 10 or 15 in which the electrical device is a transformer.

21. An article of any of claims 1, 6, 10 or 15 in which the electrical device is a capacitor and the organosilicon compound has a viscosity of from about 5 to about 50 centistokes at 25° C.

* * * * *

UNITED STATES PATENT AND TRADEMARK OFFICE
CERTIFICATE OF CORRECTION

PATENT NO. : 4,172,805
DATED : October 30, 1979
INVENTOR(S) : Gary A. Vincent

It is certified that error appears in the above-identified patent and that said Letters Patent are hereby corrected as shown below:

In Column 4, the formula number IX should read:

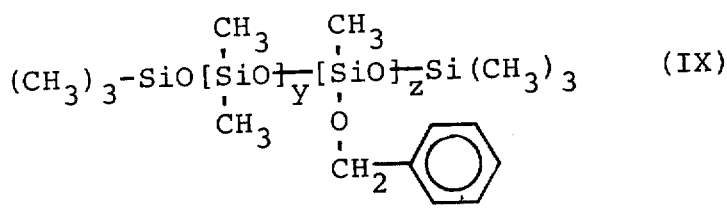

In Column 7, the second formula in Example V should read:

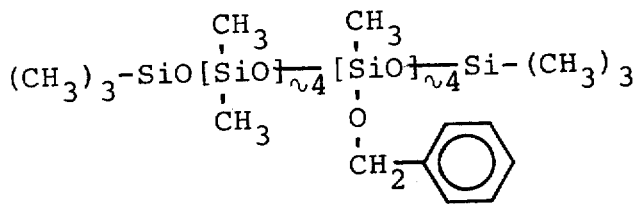

Signed and Sealed this

Twenty-eighth Day of April 1981

[SEAL]

Attest:

RENE D. TEGTMEYER

Attesting Officer

Acting Commissioner of Patents and Trademarks